(12) United States Patent
Vogt et al.

(10) Patent No.: US 6,284,081 B1
(45) Date of Patent: Sep. 4, 2001

(54) METHODS AND APPARATUS FOR APPLYING AN ELASTIC MATERIAL IN A CURVILINEAR PATTERN ON A CONTINUOUSLY MOVING SUBSTRATE

(75) Inventors: Robert Eugene Vogt; James Bennington Stopher, both of Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/471,929

(22) Filed: Dec. 23, 1999

(51) Int. Cl.[7] ........................................... A61F 13/15
(52) U.S. Cl. ................. 156/163; 156/73.1; 156/161; 156/164; 156/229; 156/494; 156/495
(58) Field of Search .................................. 156/161, 163, 156/164, 229, 494–496, 73.1

(56) References Cited

U.S. PATENT DOCUMENTS

| | | |
|---|---|---|
| 3,828,367 | 8/1974 | Bourgeois . |
| 4,293,367 * | 10/1981 | Klasek et al. ............... 156/494 |
| 4,326,528 | 4/1982 | Ryan et al. . |
| 4,486,192 | 12/1984 | Sigl . |
| 4,617,082 | 10/1986 | Oshefsky et al. . |
| 4,726,873 * | 2/1988 | Ales et al. ............... 156/495 |
| 4,909,870 | 3/1990 | Gould et al. . |
| 4,915,767 | 4/1990 | Rajala et al. . |
| 4,917,746 | 4/1990 | Kons et al. . |
| 5,091,039 | 2/1992 | Ujimoto et al. . |
| 5,110,403 | 5/1992 | Ehlert . |
| 5,275,676 | 1/1994 | Rooyakkers et al. . |
| 5,525,175 | 6/1996 | Blenke et al. . |
| 5,560,793 | 10/1996 | Ruscher et al. . |
| 5,584,954 | 12/1996 | van der Klugt . |
| 5,660,664 | 8/1997 | Herrmann . |
| 5,733,411 | 3/1998 | Bett . |
| 5,827,387 | 10/1998 | Reynolds et al. . |
| 5,871,605 | 2/1999 | Bett . |

FOREIGN PATENT DOCUMENTS

WO 96/23470  8/1996  (WO) .

* cited by examiner

*Primary Examiner*—Jeff H. Aftergut
(74) *Attorney, Agent, or Firm*—Wilhelm Law Service; Thomas D. Wilhelm; Paul Y. Yee

(57) ABSTRACT

Methods and apparatus for applying elastic material in a curvilinear pattern on a continuously moving substrate. The method moves a substrate along a substrate path, supplies the elastic material to an oscillation unit first roll mounted for pivoting and rolling engagement with a transfer roll, oscillates the oscillation unit in a path generally transverse to the substrate path, applies the elastic material from the first roll to the transfer roll in the desired curvilinear path configuration, then applies the elastic material from the transfer roll to the substrate and bonds the elastic material to the substrate. Optionally the first roll may apply the elastic material directly to the substrate. Also at least two webs of elastic materials may be applied to a continuously moving substrate in at least two curvilinear substrate paths by supplying the elastic materials to a single transfer roll, applying the elastic materials from the transfer roll to the substrate and bonding the elastic materials to the substrate.

34 Claims, 4 Drawing Sheets

METHODS AND APPARATUS FOR APPLYING AN ELASTIC MATERIAL IN A CURVILINEAR PATTERN ON A CONTINUOUSLY MOVING SUBSTRATE

FIELD OF THE INVENTION

The present invention relates to methods and apparatus for applying an elastic material, particularly wide band elastic materials, in a curvilinear pattern on a continuously moving substrate. More particularly, the present invention relates to methods and apparatus for applying wide band elastic materials in curvilinear patterns on continuously moving substrates with severe enough angular displacement to produce a composite web structure, such as a disposable diaper or other absorbent article, with regions having the attached wide band elastic materials, such as leg cuff/containment flap regions, which are more "anatomically correct".

BACKGROUND OF THE INVENTION

Conventional methods of making absorbent articles, such as disposable diapers, are well known in the art. These methods usually rely on attaching various elements to a continuously moving substrate, such as an absorbent article, as attachment materials. The elements may include leg cuffs, containment flaps or an element which is a combination leg cuff/containment flap, such as that shown in U.S. Pat. No. 5,827,387 issued Oct. 27, 1998, to Reynolds et al. The strip of attachment material may be applied to the continuously moving substrate in a discrete or continuous manner. One problem which has been encountered is the attachment of wide band elastic materials with severe enough angular displacement to provide for proper curvilinear placement. Specifically such curvilinear placement is desired to be "anatomically correct", generally in the leg opening region of an absorbent article. Thus an absorbent article having this proper curvilinear placement is perceived as having a better fit on a body of a wearer of the absorbent article.

Curving the wide band elastic attachment material has been very difficult to accomplish and practice at high speed. Manufacturers have to settle for compromises, such as making disposable diapers having straight bands of elastic, minimal angular displacement of the elastic or reducing line speed.

The application of an elastic in a curvilinear pattern to a moving web generally requires the use of rollers for positioning the strip of elastic. U.S. Pat. No. 2,592,581 to Lorig discloses a method and apparatus for positioning a strip utilizing a roll which may be cylindrical, concave, or convex as desired to suit various installations. In U.S. Pat. No. 4,081,301 to Buell adhesive is intermittently applied to the elastic material while the elastic and web substrate are continuously run at high speed. Bourgeois, U.S. Pat. No. 3,828,367, discloses that a pair of elastic ribbons are fed to curved grooves in a roll under which a continuous web passes. As the roll with the ribbons in its grooves goes over the web, the ribbons are transferred in the contoured pattern of the grooves to the roll. One problem with a grooved roll is that it is unreliable and roping and C-folding occurs with wide band elastic ribbons. U.S. Pat No. 4,917,746 to Kons et al. discloses a method and apparatus involve a single roll moving or oscillating in a single dimension to apply each elastic ribbon to a web along an undulated path. U.S. Pat No. 4,915,767 to Rajala et al. uses a rotatable nip roll to press an elastic member against the web so the elastic member is spaced a predetermined maximum distance from a dwell line, a rotatable buffer roll above and in rolling engagement with the rotatable nip roll to cushion the rotatable nip roll against transient perturbations, and an oscillating roll, oscillating in a path transverse to a direction of web travel, above and spaced apart a predetermined length from the rotatable buffer roll. The oscillating roll applies the elastic member in a curved line on the rotatable buffer roll, with the predetermined maximum distance of the elastic member from the dwell line being directly proportional to the predetermined length between the oscillating roll and the rotatable buffer roll.

The method and apparatus of the present invention allows for high speed forming of continuously moving substrates having, as attached elements, elastic materials, such as wide band elastic materials, placed with severe angular displacement in a curvilinear pattern on a continuously moving substrate by allowing a caster roller to roll and pivot while placing the elastic materials either on a transfer roll or directly on a substrate.

SUMMARY

The present invention relates to apparatus and methods for applying at least one elastic material, in a curvilinear path, onto a continuously moving substrate.

The apparatus for applying at least one web of elastic material in a curvilinear path onto a continuously moving substrate has a transporting apparatus for continuously moving the substrate along a substrate path, a rotatable transfer roll, having a transfer roll axis adapted to be in rolling engagement with the substrate and to press the elastic material against the substrate along the curvilinear path, an oscillation unit having at least a first roll having a first roll axis, the first roll being mounted for rolling engagement with a surface of the transfer roll, the first roll also mounted for pivoting about a pivot axis transverse to the surface of said transfer roll and thus being effective to apply the elastic material to said transfer roll along the curvilinear path, the pivot axis lying in a plane perpendicular to and offset from the first roll axis such that the first roll can pivot while rolling, an elastic material supply for providing the elastic material to the first roll of said oscillation unit, an oscillating drive connected to said oscillation unit for oscillating said oscillation unit in a path generally transverse to the substrate path and a bonding apparatus to secure the elastic material to the substrate along the curvilinear path when the elastic material is pressed onto the substrate by the transfer roll. Optionally the transfer roll may be deleted and the first roll may directly contact the substrate to apply the elastic material in the curvilinear path.

The method applies at least one web of elastic material in a curvilinear path onto a continuously moving substrate by moving the substrate along the substrate path, supplying the elastic material to at least a first roll having a first roll axis, the first roll being mounted for rolling engagement with a surface of said transfer roll, and for pivoting about a pivot axis transverse to the surface of said transfer roll and thus being effective to apply the elastic material to said transfer roll along the curvilinear path, the pivot axis lying in a plane perpendicular to and offset from the first roll axis such that the first roll is operative to pivot while rolling, oscillating the oscillation unit in a path generally transverse to the substrate path applying the elastic material from the first roll to the transfer roll in a curvilinear path configuration, applying the elastic material, in the curvilinear path configuration, from the transfer roll to the substrate and bonding the elastic material, in the curvilinear path configuration, to the substrate. Optionally the transfer roll may be deleted and the first roll may directly contact the substrate to apply the elastic material in the curvilinear path configuration.

An additional method contemplates applying at least two elastic materials to a single transfer roll then applying the elastic materials from the transfer roll to the substrate and bonding the elastic materials to the substrate.

Figure 1:
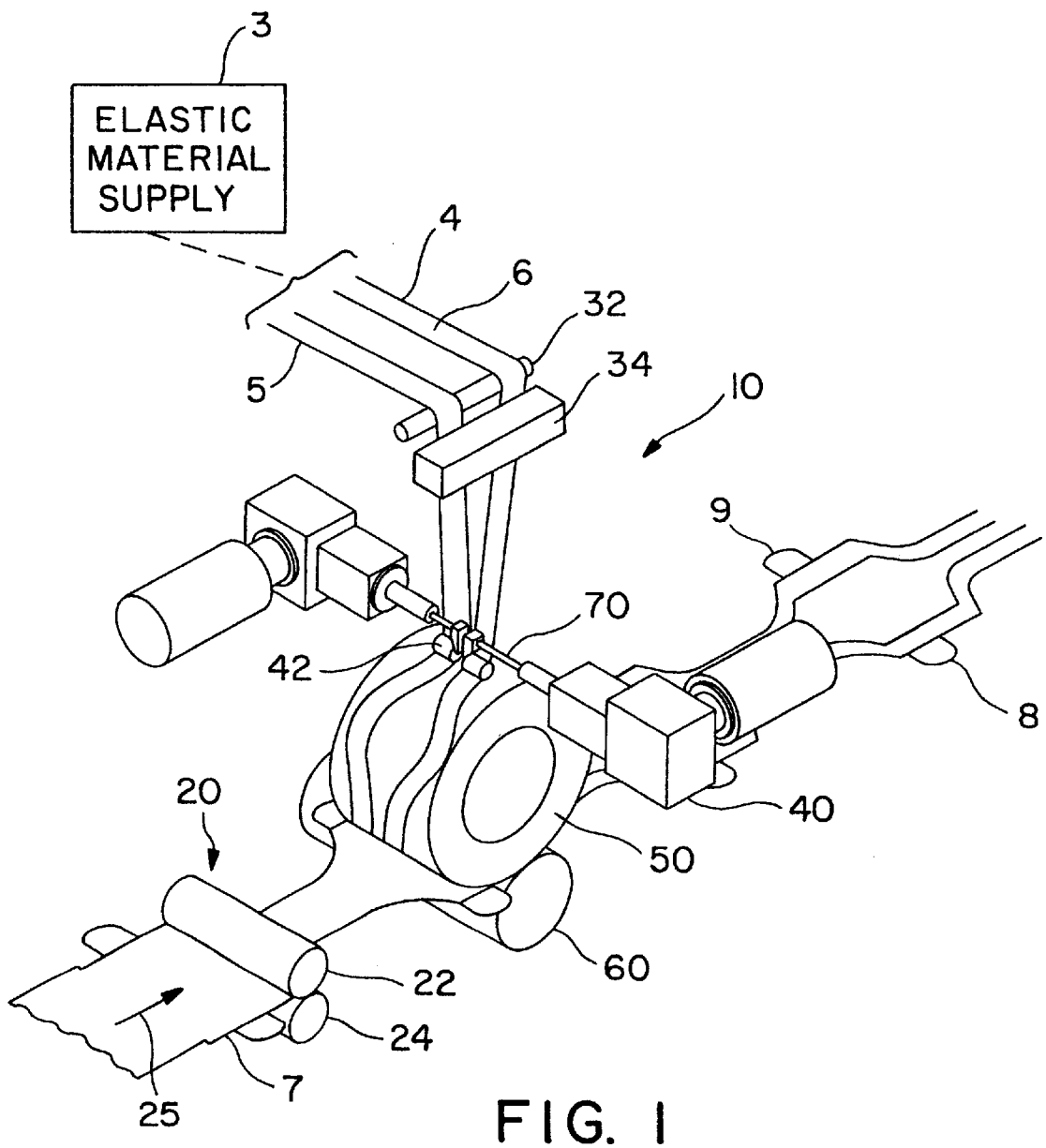
FIG. 1 shows an elevated angled view of one embodiment of an apparatus of the present invention.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

FIG. 1 shows an apparatus for applying a pair of elastic materials 4 and 5 to a substrate 7 along a curvilinear path. While a pair of elastic materials is shown, the apparatus may also be used to apply only one elastic material. For the purposes of discussion, only one of the elastic materials and its related apparatus will be discussed herein since the elastic materials and the apparatus for applying each of the elastic materials to the web are substantially identical.

Referring to FIG. 1, the elastic material 4 is relatively flat, includes wide surface 6, and has a width considerably greater than its thickness. The elastic material 4 may be supplied in any known manner that permits a continuous high speed operation. This includes pulling elastic materials, in a tangle free manner, from a box, supplying elastic materials from a reel on which the elastic materials have been wound, receiving the elastic materials directly from another processing unit which forms the elastic material or any other supply manner known in the art. Since, for the purposes of this invention, the exact manner of elastic material supply is not important, the manner of supply has not been shown. The elastic material 4 may be either in the form of a natural rubber, a synthetic elastomer or a combination of materials, such as those shown in U.S. Pat. No. 5,827,387 issued Oct. 27, 1998, to Reynolds et al. Preferably, the elastic material is a combined leg cuff and containment flap such as that detailed in U.S. Pat. No. 5,827,387 issued Oct. 27, 1998, to Reynolds et al.

As shown in FIG. 1. the apparatus 10 for applying elastic materials (4 and 5) to a substrate 7, (the substrate may also be called a web) includes a transporting apparatus 20, which may be any conventionally known type of transporting apparatus, and in FIG. 1 includes two rolls (22 and 24) for continuously moving the substrate along a substrate path as shown by the direction of substrate transport arrow 25. Attachment pieces (8 and 9) may be present on the substrate and the substrate may have other additional elements, which are not shown and will not be further discussed, depending on the exact nature of the method for preparing the article.

At least one elastic material is supplied in any known manner by an elastic material supply 3, including, as shown in FIG. 1. supplying the elastic material using a guide 32. The guide may be a roll or a bar or any other mechanism that can guide the elastic material to a first roll of an oscillation unit.

The elastic material is any band or ribbon type elastic material, however it is preferably a wide band elastic material having a width of about one half to about four inches, preferably a width of about one to about four inches and most preferably about two to about four inches.

Bonding apparatus 34 supplies adhesive at some point prior to the application of the elastic materials to the substrate. The exact positioning of the adhesive application is not critical, as long as the bonding apparatus applies the adhesive prior to the application of the elastic materials to the substrate. However, preferably the application of the adhesive should be prior to the oscillation of the elastic material to reduce the complexity of the bonding apparatus, since application of the adhesive during or after oscillation of the elastic material would also require oscillation of the bonding apparatus.

Adhesives may be of any known conventional type, so long as the adhesive causes minimal or no interference with the high speed application of the elastic materials to the substrate. One example is a pressure-sensitive adhesive.

Optionally, the bonding apparatus may be an ultrasonic unit properly positioned to be able to properly secure the elastic material to the substrate, such as, for example, at the position of a nip roll 60 in FIG. 1. For example, the ultrasonic unit and a transfer roll or a first roll may provide a nip allowing ultrasonic energy to properly secure the elastic material to the substrate. An ultrasonic unit may be a suitable generator to power an ultrasonic horn and a suitable ultrasonic horn such as a rotary ultrasonic horn taught in U.S. Pat. No. 5,110,403 to Ehlert. Alternatively, the ultrasonic horn may be a stationary ultrasonic horn as are well known to those skilled in the art.

The elastic material continues on to the oscillation unit 40 where it engages a first roll 42, also called a caster, which is a part of the oscillation unit and allows for rolling engagement of the elastic material as the elastic material is fed to the caster. The first roll is also has a pivot axis which allows pivoting while the first roll is in rolling engagement with either a transfer roll 50 or the substrate 7. Thus the caster is able to pivot at the point of rolling engagement in addition to being oscillated in a direction transverse to the direction of movement of the substrate. This allows an elastic material, preferably a wide band elastic material, to be curved with severe enough angular displacement to be perceived as more "anatomically correct" in a final article incorporating the substrate and elastic material. For example, a wide band elastic material, about one inch in width, may be applied in a sinusoidal stretched manner so that the greatest overall distance from a top edge of the wide band elastic material at the top of a sine wave to a bottom (opposing) edge of the same wide band elastic material at the bottom of the sine wave is about three and one-half inches or an angle of about sixty degrees (based on a right triangle). Preferably however the wide band elastic material is applied in an anatomically correct curvilinear pattern, rather than a mere sinusoidal pattern, with an angular displacement of any part of the anatomically correct curvilinear pattern up to and including sixty degrees.

The caster may be constructed in any manner so the elastic material remains on the caster and does not bunch up or snag upon application. The caster may have any conventionally known treated surface which facilitates the application of the elastic material. The caster shown in FIG. 2 generally has a circumferential surface 44. Pivot direction of the pivot axis is shown by pivot direction arrow 46. Preferably the caster may include a raised area or crown (not shown) encompassing part or all the circumference along part or all the length of the caster. If a crown is used, the crown is generally positioned intermediate the ends of the caster. The elastic material engages and stays on the crown as the elastic material passes around the oscillating caster. FIG. 1B in U.S. Pat. No. 4,917,746 to Kons et al., issued Apr. 17, 1990, provides an example of a roll having a crown.

An oscillating drive 70 oscillates the oscillation unit in a path generally transverse to the substrate path and is preferably a linear oscillating drive through an oscillating drive arm 72. The oscillating drive may be of a type well-known in the art and consequently will not be further described herein.

Figure 2:
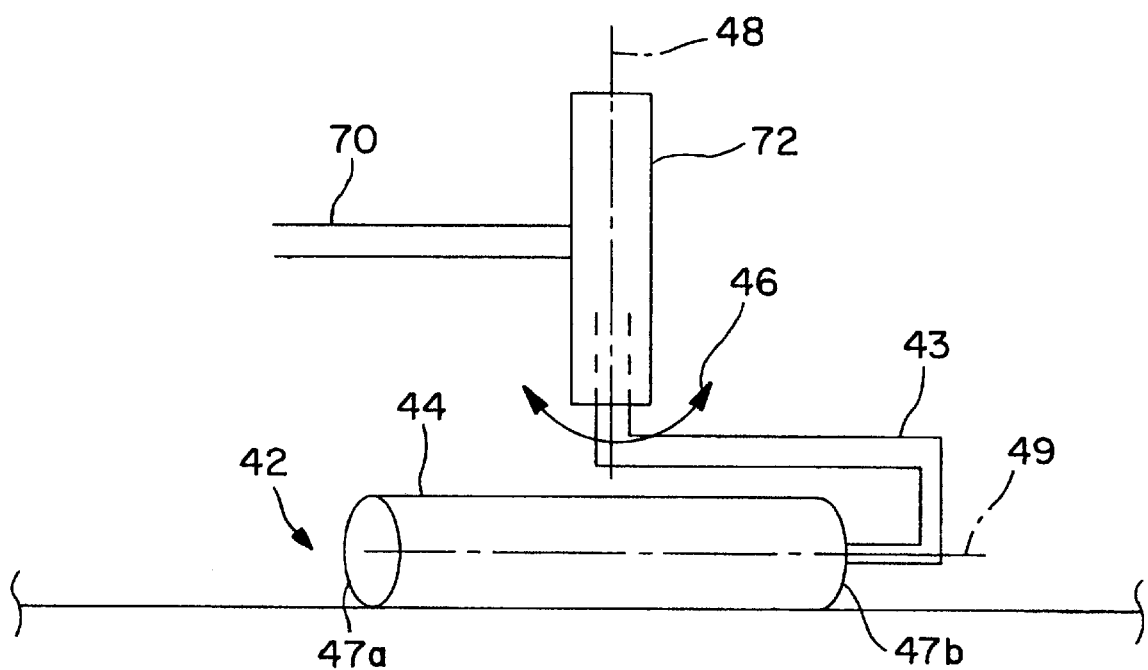
FIG. 2 shows a front view of the first roll of the oscillation unit.

Oscillating drive arm 72 is rigidly fixed to oscillating drive 70. Caster 42 must have a caster arm 43 mounted for pivotation to oscillating drive arm 72 so that the caster arm is capable of oscillating in a direction transverse to the direction of movement of the substrate and capable of pivoting about the caster arm. The caster must also be fixed to the caster arm in a manner so that the caster can pivot about a direction perpendicular to a plane tangent to the point of rolling engagement of the first roll with either the transfer roll or the substrate. FIG. 2 shows the caster in both rolling and pivoting engagement with a transfer roll. The caster may be held at either or both ends of an axis 49 (first roll axis) which allows rolling, but the caster, no matter how it is held for rolling motion, must be able to pivot as described previously. Preferably the pivot axis 48 is equidistant from both ends 47a and 47b of the caster.

Figure 3:
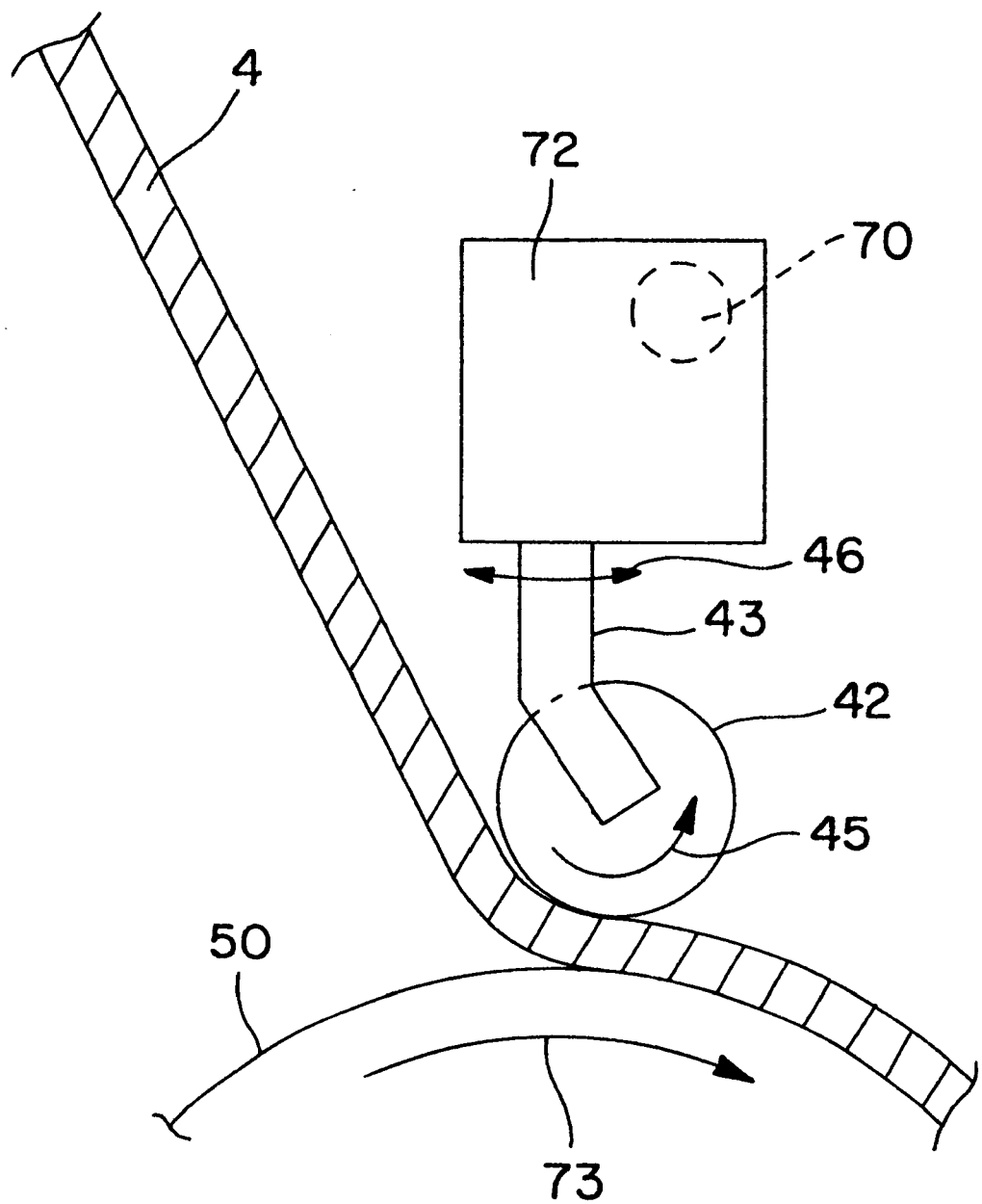
FIG. 3 shows a side view of the first roll of the oscillation unit as the elastic material is applied to the transfer roll.

FIG. 3 shows a side view of the present invention where the elastic material, after passing the guide, engages the caster and is applied to the transfer roll. FIG. 3 includes the oscillating drive arm 72 which may be directly connected to the offset caster arm 43, or both arms may be connected to an intermediate arm (not shown) to provide an offset for the caster, if necessary, so the caster may properly engage the elastic material on the caster's circumferential surface. Caster and transfer roll rolling direction arrows, 45 and 73, respectively, are also shown.

There may be other rolls in the oscillation unit, however this is not a requirement. Optionally the guide may also be part of the oscillation unit. It is a requirement that the roll that is actually in engagement with either the transfer roll or the substrate be in both rolling and pivoting engagement with the transfer roll or substrate.

The caster, with the engaged elastic material, is in rolling and pivoting engagement with either the transfer roll 50 in one embodiment or directly with the substrate 7 in a second embodiment. The elastic material is then transferred from the caster to either the transfer roll in a curvilinear configuration and then applied to the substrate (FIG. 1) or directly to the substrate in a curvilinear configuration.

The transfer roll, with the engaged curvilinear elastic material, is in rolling engagement with the substrate, and rotates to apply the elastic material to the substrate in the desired curvilinear pattern. A nip roll 60 working in rolling cooperation with the transfer roll or the caster, assists the transfer roll, or the caster, in placing the elastic material onto the substrate with a desired amount of pressure to properly secure the elastic material to the substrate in the desired curvilinear pattern. Optionally, transfer roll/nip roll configuration may include or be replaced by the bonding apparatus in the form of an ultrasonic unit able to properly secure the elastic material at the location where the elastic material is applied to the substrate. Also while it is possible to use multiple transfer rolls in the present invention, it is less complex and therefore preferable to utilize only a single transfer roll, even when utilizing multiple casters as is shown in FIG. 1.

The transfer roll may also be a variable velocity roll, with or without a hot knife, or other type of cutting roll such that the elastic material is curved, held, cut and applied in discrete units in the desired curvilinear manner. Other conventional measures, such as vacuum and/or roll surface coatings, may be used in conjunction with the transfer roll to keep the elastic material engaged on the transfer roll.

After passing through the nip defined by the transfer roll and nip roll or the caster and nip roll, the substrate with the attached curvilinear elastic material continues on the substrate path for further processing.

Figure 4:
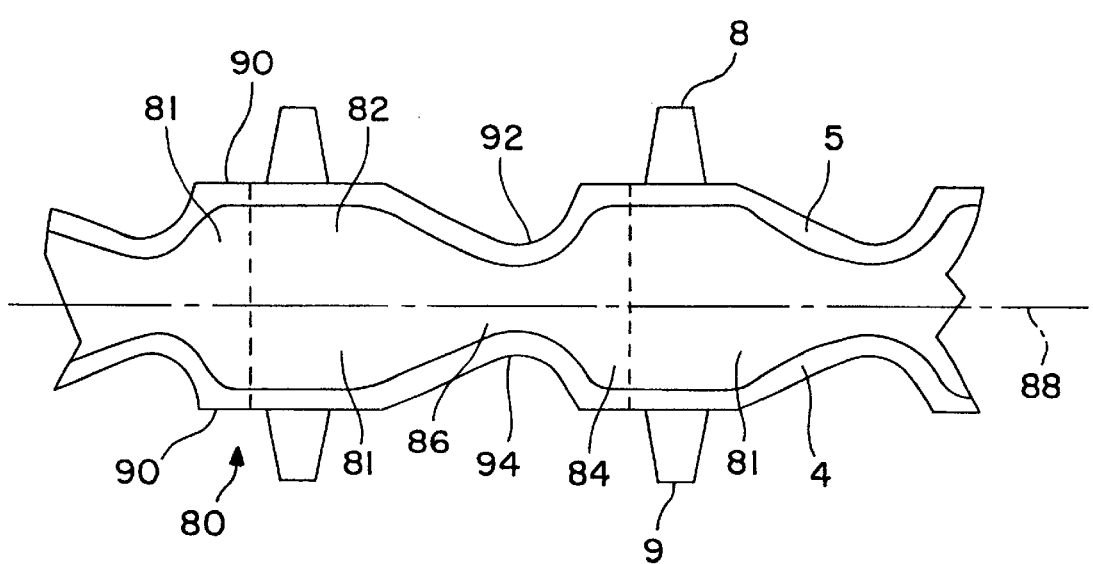
FIG. 4 shows an overhead view of the composite web structure.

The substrate with the attached elastic materials 4 and 5 is a composite web structure 80. As shown in FIG. 4, each workpiece 81 on this composite web structure has a rear portion 82, a front portion 84, and a narrower crotch portion 86 between the front and rear portions, corresponding to respective front, rear and crotch portions of personal care absorbent articles made from the respective workpieces. A longitudinal axis 88 extends through the front, rear and crotch portions. Longitudinal edge 90 have leg cutouts 92 and 94, generally in the shape of a "J" with the curved part of the "J" being disposed toward the front portion of the respective workpiece. The elastic materials (4 and 5) are stretched, curved and placed so that they match the "J" profile which is narrower in the front portion of the composite web structure and has an increased width towards the rear portion of the composite web structure to provide a more "anatomically correct" fit. The "J" profile is considered to be more anatomically correct than a mere sinusoidal or circular profile often used for leg cutouts.

Preferably the elastic materials define the previously described leg cuff/containment flap elastic materials.

Several advantages are obtained from the present apparatus, method and composite web structure. First, the overall apparatus is not complex. Second, this apparatus and method allows high speed (i.e. greater than 300 workpieces per minute) placement of wide band elastic materials onto a substrate, while third, allowing more severe angular displacement of the elastic material, with respect to the substrate path 25, in the composite web structure to achieve a better fit of the final article about the body of the wearer.

The substrate and elastic material composite may be stored for later use in any known manner or alternatively, the composite may be used immediately in the fabrication of disposable garments such as disposable diapers. When used in a disposable diaper, the curved elastic in each individual diaper fabricated from the substrate and elastic material composite provides elastic materials which are contoured to fit the shape of the body on which the diaper is worn and thereby provide a better fit or seal of the diaper against the body. Moreover, the benefit of the method and apparatus of this invention may be obtained while manufacturing elasticized disposable diapers or other disposable garments at very high production speeds and having severe elastic material angular placement.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A method for applying at least one web of elastic material in a curvilinear path onto a continuously moving substrate, said method comprising:
   (a) moving the substrate along the substrate path;
   (b) supplying the elastic material to an oscillation unit having at least a first roll having a first roll axis, said first roll being mounted for rolling engagement with a surface of a transfer roll, and said first roll pivoting about a pivot axis transverse to the surface of said transfer roll and thus being effective to apply the elastic material to said transfer roll along the curvilinear path, the pivot axis lying in a plane perpendicular to and offset from the first roll axis such that the first roll is operative to pivot while rolling;
   (c) oscillating the oscillation unit in a path generally transverse to the substrate path;
   (d) applying the elastic material from the first roll to the transfer roll in a curvilinear path configuration;
   (e) applying the elastic material, in the curvilinear path configuration, from the transfer roll to the substrate; and
   (f) bonding the elastic material, in the curvilinear path configuration, to the substrate.

2. A method as recited in claim 1 wherein the oscillating of the oscillation unit comprises linearly oscillating the oscillation unit in a path generally transverse to the substrate path.

3. A method as recited in claim 1 wherein the bonding of the elastic material to the substrate comprises applying adhesive to the elastic material upstream of the first roll such that the adhesive contacts the substrate and thereby secures the elastic material to the substrate when the elastic material is applied onto the substrate by the transfer roll.

4. A method as recited in claim 1 wherein the supplying of the elastic material to the first roll of the oscillation unit comprises guiding the elastic material about to a guide prior to supplying the elastic material to the first roll of the oscillation unit.

5. A method as recited in claim 1 wherein the supplying of the elastic material to the first roll of the oscillation unit comprises guiding the elastic material about an oscillation unit guide prior to supplying the elastic material to the first roll of the oscillation unit.

6. A method as recited in claim 1 wherein the supplying of the elastic material to the first roll of the oscillation unit comprises supplying a combined leg cuff and containment flap material to the first roll of the oscillation unit.

7. A method as recited in claim 1 comprising supplying the elastic material from the first roll to a variable velocity vacuum transfer roll.

8. A method as recited in claim 1 further comprising nipping the elastic material and the substrate between the transfer roll and a nip roll.

9. A method as recited in claim 1 wherein the bonding of the elastic material to the substrate is through use of an ultrasonic bonding apparatus.

10. A method for applying at least one web of elastic material in a curvilinear path onto a continuously moving substrate, said method comprising:
    (a) moving the substrate along the substrate path;
    (b) supplying the elastic material to an oscillation unit having at least a first roll having a first roll axis, said first roll being mounted for rolling engagement with a surface of said substrate, and said first roll pivoting about a pivot axis transverse to the surface of said substrate and thus being effective to apply the elastic material to said substrate along the curvilinear path, the pivot axis lying in a plane perpendicular to and offset from the first roll axis such that the first roll is operative to pivot while rolling;
    (c) oscillating the oscillation unit in a path generally transverse to the substrate path;
    (d) applying the elastic material from the first roll to the substrate in the curvilinear path configuration; and
    (e) bonding the elastic material, in the curvilinear path configuration, to the substrate.

11. A method as recited in claim 10 wherein the oscillating of the oscillation unit comprises linearly oscillating the oscillation unit in a path generally transverse to the substrate path.

12. A method as recited in claim 10 wherein the bonding of the elastic material to the substrate comprises applying adhesive to the elastic material upstream of the first roll such that the adhesive contacts the substrate and thereby secures the elastic material to the substrate when the elastic material is applied onto the substrate by the first roll.

13. A method as recited in claim 10 wherein the supplying of the elastic material to the first roll of the oscillation unit comprises guiding the elastic material to a guide prior to supplying the elastic material to the first roll of the oscillation unit.

14. A method as recited in claim 10 wherein the supplying of the elastic material to the first roll of the oscillation unit comprises guiding the elastic material to an oscillation unit guide prior to supplying the elastic material to the first roll of the oscillation unit.

15. A method as recited in claim 10 wherein the supplying of the elastic material to the first roll of the oscillation unit comprises supplying a combined leg cuff and containment flap material to the first roll of the oscillation unit.

16. A method as recited in claim 10 further comprising nipping the elastic material and the substrate between the first roll and a nip roll.

17. A method as recited in claim 10 wherein the bonding of the elastic material to the substrate is through use of an ultrasonic bonding apparatus.

18. Apparatus for applying at least one web of elastic material in a curvilinear path onto a continuously moving substrate, said apparatus comprising:
    (a) transporting apparatus for continuously moving the substrate along a substrate path;
    (b) a rotatable transfer roll, having a transfer roll axis, and being adapted to be in rolling engagement with the substrate and to press the elastic material against the substrate along the curvilinear path;
    (c) an oscillation unit having at least a first roll having a first roll axis, said first roll being mounted for rolling engagement with a surface of said transfer roll, and said first roll pivoting about a pivot axis transverse to the surface of said transfer roll and thus being effective to apply the elastic material to said transfer roll along the curvilinear path, the pivot axis lying in a plane perpendicular to and offset from the first roll axis such that the first roll is operative to pivot while rolling;

(d) an elastic material supply providing the elastic material to said first roll of said oscillation unit;

(e) an oscillating drive connected to said oscillation unit and oscillating said oscillation unit along a path generally transverse to the substrate path; and (f) bonding apparatus securing the elastic material to the substrate along the curvilinear path when the elastic material is pressed onto the substrate by said transfer roll.

19. Apparatus as recited in claim 18 wherein the oscillating drive is a linear oscillating drive which oscillates in a path generally transverse to the substrate path.

20. Apparatus as recited in claim 18 wherein said bonding apparatus comprises an adhesive applicator which applies adhesive to the elastic material upstream of said first roll such that the adhesive contacts the substrate and thereby secures the elastic material to the substrate when the elastic material is pressed onto the substrate by said transfer roll.

21. Apparatus as recited in claim 18 further comprising a guide between the elastic material supply and the first roll guiding the elastic material to the first roll of the oscillation unit.

22. Apparatus as recited in claim 21 wherein said oscillation unit includes said guide.

23. Apparatus as recited in claim 18 wherein said elastic material supply is a combined leg cuff and a containment flap material supply.

24. Apparatus as recited in claim 18 wherein said transfer roll is a variable velocity vacuum transfer roll.

25. Apparatus as recited in claim 18 wherein said bonding apparatus further comprises a nip roll to help secure the elastic material to the substrate.

26. Apparatus as recited in claim 18 wherein said bonding apparatus further comprises an ultrasonic apparatus securing the elastic material to the substrate.

27. Apparatus for applying at least one web of elastic material in a curvilinear path onto a continuously moving substrate, said apparatus comprising:

(a) transporting apparatus for continuously moving the substrate along a substrate path;

(b) an oscillation unit having at least a first roll having a first roll axis, said first roll being mounted for rolling engagement with the substrate, and said first roll pivoting about a pivot axis transverse to the surface of said substrate and thus being effective to apply the elastic material to the substrate along the curvilinear path, the pivot axis lying in a plane perpendicular to and offset from the first roll axis such that the first roll is operative to pivot while rolling;

(c) an elastic material supply for providing the elastic material to said first roll of said oscillation unit;

(d) an oscillating drive connected to said oscillation unit and oscillating said oscillation unit along a path generally transverse to the substrate path; and (e) a bonding apparatus securing the elastic material to the substrate along the curvilinear path when the elastic material is pressed onto the substrate by said transfer roll.

28. Apparatus as recited in claim 27 wherein the oscillating drive is a linear oscillating drive which oscillates in a path generally transverse to the substrate path.

29. Apparatus as recited in claim 27 wherein said bonding apparatus comprises an adhesive applicator which applies adhesive to the elastic material upstream of said first roll such that the adhesive contacts the substrate and thereby secures the elastic material to the substrate when the elastic material is pressed onto the substrate by said first roll.

30. Apparatus as recited in claim 27 further comprising a guide between the elastic material supply and the first roll guiding the elastic material to the first roll of the oscillation unit.

31. Apparatus as recited in claim 30 wherein said oscillation unit includes said guide.

32. Apparatus as recited in claim 27 wherein said elastic material supply is a combined leg cuff and a containment flap material supply.

33. Apparatus as recited in claim 27 wherein said bonding apparatus further comprises a nip roll to help secure the elastic material to the substrate.

34. Apparatus as recited in claim 27 wherein said bonding apparatus further comprises an ultrasonic apparatus securing the elastic material to the substrate.

* * * * *